United States Patent [19]
Loeb

[11] Patent Number: 5,312,439
[45] Date of Patent: May 17, 1994

[54] IMPLANTABLE DEVICE HAVING AN ELECTROLYTIC STORAGE ELECTRODE

[76] Inventor: Gerald E. Loeb, 90 Bagot Street, Kingston, Ontario, Canada, K7L 3E5

[21] Appl. No.: 806,584

[22] Filed: Dec. 12, 1991

[51] Int. Cl.⁵ ............................................. A61N 1/05
[52] U.S. Cl. .................................. 607/2; 607/61; 607/1; 607/116
[58] Field of Search ............... 128/419 PS, 783, 784, 128/421, 419 R

[56] References Cited

U.S. PATENT DOCUMENTS

| | | | |
|---|---|---|---|
| 4,440,178 | 4/1984 | Bussard et al. | 128/784 |
| 4,934,368 | 6/1990 | Lynch | 128/419 R |

OTHER PUBLICATIONS

Mindt et al., "Stimulating Electrode with Low Energy Consumption", Med. & Biological Eng., Sep. 1973, vol. 11, No. 5.
Guyton et al., "Theory & Design of Capacitor Electrodes for Chronic Stimulation," Med. & Biolg. Eng. Sep. 1974, vol. 12, pp. 613-619.
Hildebrandt et al., 7th Int. Symp. on External Cntrl. of Human Extremities, "Neuromuscular Funct. Stim. by Miniaturized Impl. Elect. Stim." Dubrovnik, Yug, Sep. 1981.
Robblee et al., "Activated Ir: An Elect. Suitable for Revers, Charge Inject. in Saline Soln," J. Electrochemical Soc., vol. 130, pp. 731-733, 1983.
Rose et al., "Assessment of Cap. Elect. for Intracortical Neural Stim.," J. of Neuroscience Methods, vol. 12, 1985, pp. 181-193.

*Primary Examiner*—William E. Kamm
*Assistant Examiner*—Kennedy J. Schaetzle
*Attorney, Agent, or Firm*—L. Lee Humphries

[57] ABSTRACT

An electrolytic, capacitive electrode, adapted to be disposed in body fluids when implanted, is used to store electrical energy for use in providing electrical energy to at least a portion of the internal electrical circuitry of an implantable device. Substantial capacitance is provided, particularly when constructed of anodized, porous tantalum with a counterelectrode of activated iridium. Such capacitive electrodes, exposed outside the implantable device, alleviate the requirement for space for a storage capacitor within miniature, implantable devices and may also serve as stimulating electrodes.

38 Claims, 4 Drawing Sheets

IMPLANTABLE DEVICE HAVING AN ELECTROLYTIC STORAGE ELECTRODE

This invention relates to an implantable device using one or more exposed, electrolytic electrodes to store electrical energy received by the implanted device, for the purpose of providing electrical energy to at least a portion of the internal electrical circuitry of the implantable device. Such an exposed electrode provides substantial capacitance by being immersed in the body fluids and acting as an electrolytic capacitor. Further, such external, electrolytic capacitance alleviates the requirement for space by such capacitance within miniature and microminiature, implantable devices. Also, the electrode may be further used as a stimulating electrode.

Such an electrolytic electrode is particularly advantageous in a microminiature, implantable stimulator, which may be implanted through the lumen of a hypodermic needle.

This invention is related to two other patent applications filed on Dec. 18, 1991, and issued on Mar. 16, 1993, as U.S. Pat. No. 5,193,539 for Implantable Microstimulator and U.S. Pat. No. 5,193,540 for Structure and Method of Manufacture of Implantable Microstimulator. The inventor herein is a joint inventor in those two issued patents. Reference to such patents may be made to obtain helpful information and technical background for the construction of the implantable device described herein.

BACKGROUND

Electrical storage devices in implantables are usually batteries, which may or may not be rechargeable. Capacitances have been used within implanted devices for various purposes, such as to provide signal demodulation, detection, filtering, and to remove unwanted alternating currents, but it is not believed that electrolytic, capacitive electrodes. disposed in body fluids, have been previously used to store the electrical energy needed for operating the internal electrical circuitry of an implantable device.

Various investigators have used an electrolytic, capacitor electrode to conduct electrical energy for a stimulating pulse. An article by Guyton and Hambrecht, entitled "Theory and design of capacitor electrodes for chronic stimulation", in Medical and Biological Engineering, Sep. 1974, page 613 and following, discloses and discusses such a system. In that case, the electrode also serves as the stimulating electrode. A counterelectrode, which adds to the storage capacitance, has also been used with such electrolytic, capacitor electrode, and such counterelectrode has also served as the other, stimulating electrode.

U.S. Pat. No. 4,934,368, for Multi-Electrode Neurological Stimulation Apparatus, inventor, H. Wilfred Lynch, shows, in FIG. 19, a storage capacitor which provides electrical energy to control and demultiplexing electronics, which includes a shift register. An electrolytic storage capacitor, disposed in body fluids, is not suggested. It is proposed in that patent that the capacitor be kept small so as not to interfere with the stimulating pulse.

SUMMARY OF THE INVENTION

The electrolytic, capacitor electrode is particularly useful in miniature, implantable devices because of its ability to store a large amount of electrical energy in a small electrode. It is particularly useful in microminiature implants where an external electrode is required for electrical stimulation. The same electrode can be used as the electrolytic, storage capacitor electrode.

The electrolytic, capacitor electrode is used with a counterelectrode which, preferably, adds to the capacitance of the implanted device.

The electrolytic, capacitive electrode, disposed in body fluids, is capable of providing power to all, or a portion, of any of the electrical circuitry within an implanted device. For example, the electrical circuitry, powered in whole or in part by such electrolytic, capacitive electrode or electrodes, may be the operating electronics, the control electronics or the data processing electronics. In distinction to the filter capacitor of a power supply, in which the input and output currents are essentially equal, the capacitor means in the device of the invention is utilized to provide output currents at a rate substantially in excess of the rate at which the implantable device receives the electrical energy.

It is therefore an object of this invention to provide an implantable device comprising an electrolytic, capacitive electrode, exposed to body fluids, when implanted, and adapted to store electrical energy for powering the internal electrical circuitry of such implantable device.

A further object of this invention is to provide an implantable device comprising an electrolytic, capacitive electrode and a counterelectrode, exposed to body fluids, when implanted, and adapted to store electrical energy for powering the internal electrical circuitry of such implantable device.

A further object of this invention is to provide a implantable device comprising an electrolytic, capacitive electrode of an anodized, porous metal, adapted to be exposed to body fluids when implanted and provide capacitor means for the storage of at least a portion of the electrical energy used by the internal electrical circuitry of said implantable device.

A still further object of this invention is to provide an implantable device comprising an electrode of activated iridium, adapted to be exposed to body fluids when implanted and provide capacitor means for the storage of at least a portion of the electrical energy used by the internal electrical circuitry of said implantable device.

DESCRIPTION OF THE DRAWINGS

Other objects and features will be apparent from the following description and drawings in which.

DETAILED DESCRIPTION OF THE INVENTION

Figure 1:
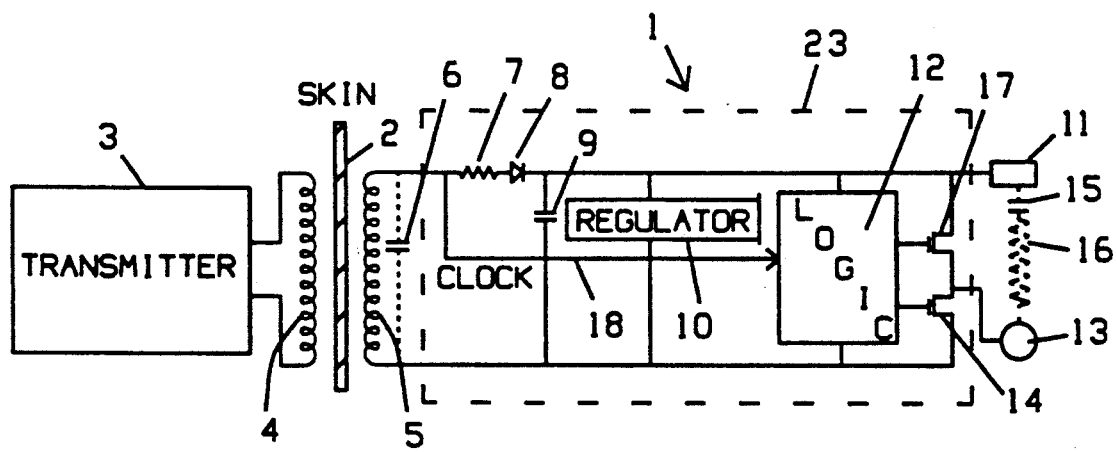
FIG. 1 is a schematic of an implantable stimulator showing two electrodes connected in electrical circuit and controlled by logic electronics.

In FIG. 1 is shown an example of the application of the invention to an implantable stimulator. The implanted device 1 receives electrical energy through the skin 2 from a transmitter 3. Inductive coil 4 provides an alternating magnetic field which is inductively or otherwise coupled to receiving coil 5.

The transmitter 3 for driving coil 4 is, preferably, a class E driver. Such class E drivers are well-known in the art and an analysis of them may be found in an article entitled, *"Exact Analysis of Class E tuned Power Amplifier at any Q and Switch Duty Cycle,"* Kazimierczuk and Puczko. IEEE Transactions on Circuits and Systems, Vol. CAS-34, No. 2 February, 1987, pp. 149-159. Numerous additional references are therein cited. Inductive transdermal links are further disclosed and discussed in U.S. Pat. No. 4,679,560, for Wide Band Inductive Transdermal Power and Data Link, inventor, Douglas C. Galbraith.

Capacitor 6 may be a discrete capacitor or may be the distributed capacitance of coil 5, depending on the particular situation.

Resistor 7 and rectifying diode 8 provide electrical energy which is stored on capacitor 9, whose voltage is regulated by regulator 10. The voltage on one side of capacitor 9 is also connected to electrode 11. The voltage on the other side of capacitor 9 is connected, under the control of logic 12, to electrode 13, through transistor switch 14.

Electrode 11 is anodized, porous tantalum, in the preferred embodiment and is preferably operated anodally. The electrode 11 becomes an electrolytic capacitive electrode when immersed in body fluids. Other porous metals may be used. What is desired is a high surface-to-volume ratio in order to provide as much surface area as possible in the electrode. Such a large surface area may be achieved by one or more of sintering, electro-reduction etching, sputtering, and build-up of rough, electroplated surfaces.

Electrode 13 is activated iridium, in the preferred embodiment, and is preferably operated cathodally. Electrodes 11 and 13, when immersed in body fluids, provide a very large capacitance between them. Such capacitance is represented at 15 and may easily be on the order of a hundred or so microfarads. Resistor 16 represents the few hundred ohms of body resistance between the two electrodes.

After the capacitor 15 is charged, it may be discharged totally or partially, to provide a stimulating pulse, through transistor switch 17. Such stimulating pulse may be synchronized with other devices, through clock signals received by logic 12 on line 18. A stimulating pulse would require a small portion of the energy that could be stored on the capacitor 15

Figure 2:
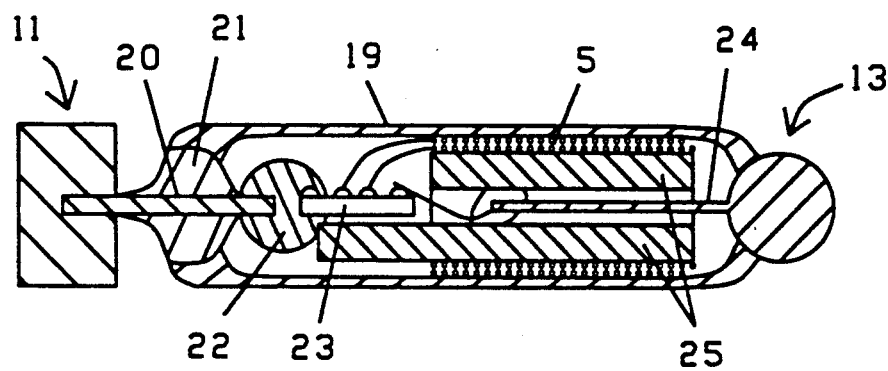
FIG. 2 is a cross-section of an microminiature, implantable stimulator showing a electrode at each end.

The physical structure of a microminiature, implantable stimulator is shown in cross-section in FIG. 2. Electrode 11 is at one end and electrode 13 is at the other end of an inert, hermetically-sealed housing 19. Such housing 19 may be, for example, capillary glass tubing, ceramic or other suitable material. In a microminiature device, for example, the glass tubing would be approximately 10 mm long and have an outer diameter of approximately 2 mm. Such a size would allow implanting the device through the lumen of a hypodermic needle. Such glass capillary tubing is preferably a biocompatible, lime glass or borosilicate glass, such as N51A soda-lime glass, and is commonly available from or through glass fabrication houses such as Kimbel Glass or Corning Glass. Two requirements of the glass are that it be inert when implanted and that it have a temperature coefficient of expansion approximately equal to that of the electrodes if it is to be hermetically sealed to the electrodes by heat.

Heat sink fixtures and shields may be used in the sealing process to protect the electrodes, particularly the porous electrodes which are prone to burn when exposed to high temperatures.

The stem 20 of electrode 11 extends through a hermetic seal 21, which may be a glass bead or washer, which is first fused to stem 20 and then fused to the housing 29. Stem 20 is connected by conductive epoxy 22 to electronic circuit chip 23. As may be seen in FIG. 1, electronic circuit chip 23 contains the electronics of the implanted device. Chip 23 is, preferably, high speed, low current, silicon-gate CMOS which has low power requirements and can be readily obtained in microminiaturized form Electrode 13 is directly sealed to the glass housing and its stem 24 extends into housing 19 and is electrically connected to electronic circuit chip 23.

Coil 5 is also connected to electronic circuit chip 23 as shown in both FIGS. 1 and 2. Coil 5 may be several hundred turns wound around a ferrite core 25. Stem 24 extends through a tunnel in ferrite core 25.

Figure 3:
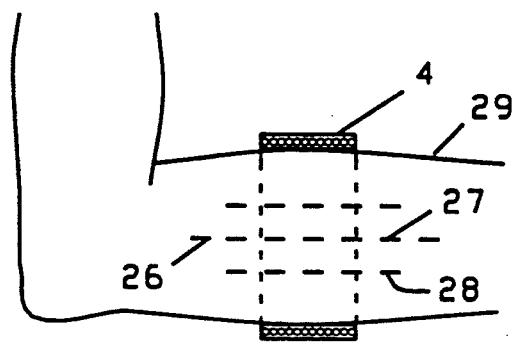
FIG. 3 is an illustration of several microminiature devices implanted in an arm.

FIG. 3 illustrates how a number of implants 26, 27 and 28 might be placed in an arm 29. The transmitter coil 4 is shown encircling the arm, to provide power to the implants.

Figure 4:
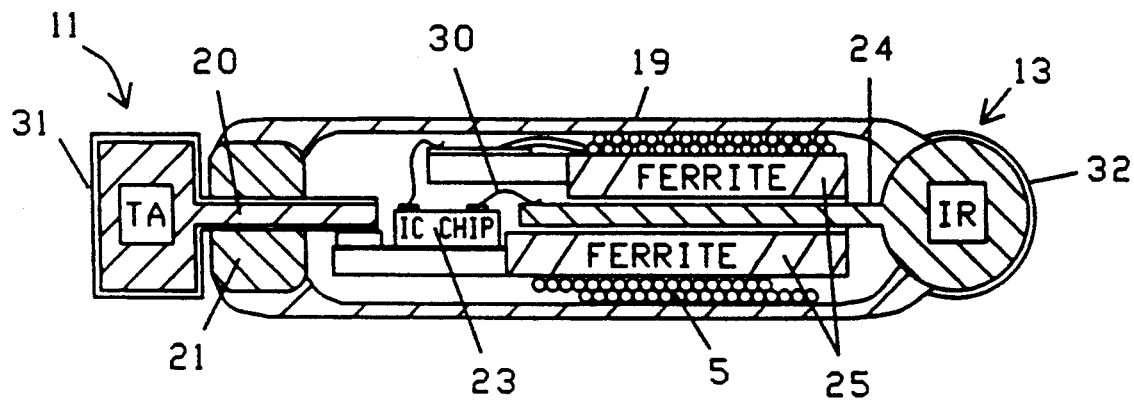
FIG. 4 is a cross-section of a microminiature device showing an anodized layer on one electrode and an activated layer on the other and how the electrodes are connection internally to other structure and electrical circuits.

FIG. 4 is a cross-section of a microminiature device showing an anodized layer 31 electrode 11 and an activated layer 32 on electrode 13 and how the electrodes are connected internally to other structure and electrical circuits. Stem 24 is shown connected to electronic circuit chip 23 by wire 30.

Electrode 11, in a microminiature, preferred embodiment, is constructed of powdered tantalum metal molded and sintered into a pellet on the end of a 0.25 mm diameter wire, tantalum stem 20. Before anodizing, the tantalum electrode, is cleaned by stripping the oxide from it in a bath of HF acid. The stem is given a diamond polish, where it passes through glass bead 21 to remove the scratches and nicks. The tantalum stem 20 is threaded through the glass bead 21 of N51A soda-lime glass and the portion of the stem protruding inside the glass bead is gold plated (plating not shown). Glass bead 21 is first fused to stem 20 and then fused to the housing 29. Electrode 11 is anodized to form a thin anodized layer 31. This may be done prior to, but is preferably done after the housing is sealed to the glass bead because the heat of sealing to the glass bead and to the housing may affect the anodization. In a microminiature construction, the glass bead may be of the size of the tantalum pellet, approximately 0.060" in diameter and 0.042" in width. The entire length of the tantalum electrode is approximately 0.110". The porous nature of the pellet allows intimate relationship with the body fluids, but is of sufficiently small cellular structure that fibrous growth does not occur within the cells. The pellet is the outer, exposed portion of the electrode and is formed as a cylindrical section approximately less than 2 mm long and 2 mm in diameter, (approximately 6 or 7 mm:). The outer exposed pellet comprises, by its porous structure and anodized layer, an electrolytic capacitor, shown as capacitor 15, FIG. 1, with resistance 16 illustrating the resistance of the path through the body, approximately 300 ohms, between the electrodes 11 and 13. The electrolytic capacitance of capacitor 15, provided by tantalum electrode 11 and iridium counterelectrode 13, can be significant even in such miniature forms, being on the order of 2 to 30 microfarads. For greater capacitance, the outer cylindrical section of tantalum electrode 15 and the iridium ball electrode 13 can be larger, but it is expected that sufficient capacitance can be achieved in the tantalum electrode 13 by a volume of 7 mm$^3$. It has been found by others that anodized tantalum has a very low DC leakage level when biased up to 80% of the anodization voltage and tends to self-heal in body fluids.

Electrode 13, which is spherical in one embodiment, is formed of iridium wire. The iridium ball and stem are formed by melting a 0.006" or 0.010" iridium wire such that it forms a ball at the end of the wire. The wire may be lowered vertically into the tip of an oxy-acetylene flame and the iridium will melt and retract to form a ball on the end of the stem. Too large a ball will fall off. Care is taken during rapid cooling to center the ball on the stem. Ball diameters were tested from 0.038" (0.97 mm) to 0.050" (1.25 mm), just slightly smaller than the inner diameter of the 2 mm D glass tubing, and it was found that the larger ball sealed quicker and were easier to keep centered and gave a longer seal path. The preferred diameter is 0.060".

One side of the iridium ball is remelted, prior to its assembly, to present a very smooth surface for fusing to the housing 22. The iridium electrode is cleaned by reduction in a saline solution with 3 to 6 volts applied and then may be readily fused to the housing.

In the manufacturing process of electrode 13 and its activated layer, the exposed surface of electrode 13 (which is preferably iridium) is activated by immersing it in a phosphate-buffered saline solution and touching its outside surface with a whisker probe, (fine iridium wire of 0.003" D), and cycling for 20 to 30 minutes at 0.5 volts per second to a maximum of plus or minus 0.8 volts. The cyclic voltammetry builds up an electrically conductive layer of iridium hydrous oxide, layer 14A, (an activated layer), that is capable of being cycled reversibly between the +3 and +4 valence states, thereby transforming electron motion in the underlying metal into ion fluxes in the surrounding solution without inducing irreversible electrolysis of the water or metal. The interfacial impedance tends to be very low, also, reducing the necessary voltage between the electrodes 14 and 15 to be used in obtaining stimulation.

In operation, the tantalum electrode 11 may be charged to +15 volts, with the iridium electrode 13 providing a counter electrode. Upon discharge, or partial discharge of the charge, due to a stimulating pulse, the tantalum electrode 11 may drop substantially in voltage, say, to 8 volts, but the iridium electrode 13 remains at approximately −0.4 volts. The combination of tantalum and iridium allow the tantalum to be charged to a high voltage, necessary for the stimulating pulse.

Such electrode 11, although it may only be 1.5 mm on a side, will easily store 100 microcoulombs of charge. Only 3.84 microcoulombs of charge is required for a 15 ma stimulating pulse having a 256 microsecond duration. Furthermore, the charge may be stored at a voltage (say, 10 volts or larger) sufficient to overcome the output impedance (approximately 300 ohms) of the two electrodes and the intervening tissues of the body. Upon the largest stimulation pulse, the voltage between the electrodes 14 and 15 may drop to 8 volts, for example.

Other metals may be used for each of the electrodes, but the above are the preferred. Some of the other metals which may be used, in their porous or non-porous forms for one or the other of the electrodes, are chromium, cobalt, hafnium, indium, iridium, molybdenum, niobium, palladium, platinum, silver, stainless steel, titanium, tungsten, vanadium, zirconium, and various combinations and alloys of the above. The inner pores of the Porous electrode may be plated, electrically or chemically, in combination with an electrically-conductive material other than the porous material. The surface layers may also be a carbide, nitride or carbonitride layer. U.S. Pat. No. 4,611,604, for Bipolar Electrode for Medical Applications, inventor, Lars Botvidsson and Konrad Mund, teaches using a layer of activated carbon on a porous surface or at least a roughened surface.

The choice of the counter-electrode is actually quite critical. In effect, the system acts like two capacitors in series, so the capacitance of the counterelectrode must be even higher to avoid limiting the effective charge storage capacitance. Total capacitance in a series circuit is $1/(1/C_1 + 1/C_2)$, like resistors in parallel. If two, symmetrical tantalum electrodes were used, one would be charged anodically (with respect to body fluids) and the other cathodally, which would cause the latter to fail. Activated iridium acts like a very large capacitor during brief pulses but it is non-polarizing in the long term because it slowly changes the distribution of $Ir+3$ and $Ir+4$ atoms in the oxide layer in response to applied currents. The Ir-saline-Ta electrode system always floats to a distribution of metal-electrolyte potentials in which the Ir is at about −0.4 V vs. standard calomel electrode (SCE) while the rest of the applied DC potential (typically 8-10 volts) appears as a positive potential on the Ta vs. SCE. This is exactly what is required to maintain an anodic bias on the Ta and to keep the potential excursions of the Ir operating around zero volts, where water electrolysis cannot occur and the iridium oxide layer is highly conductive. There are other metals that can be used as the counterelectrode (rhodium, for example), but they must have this non-polarizing property.

Figure 5:
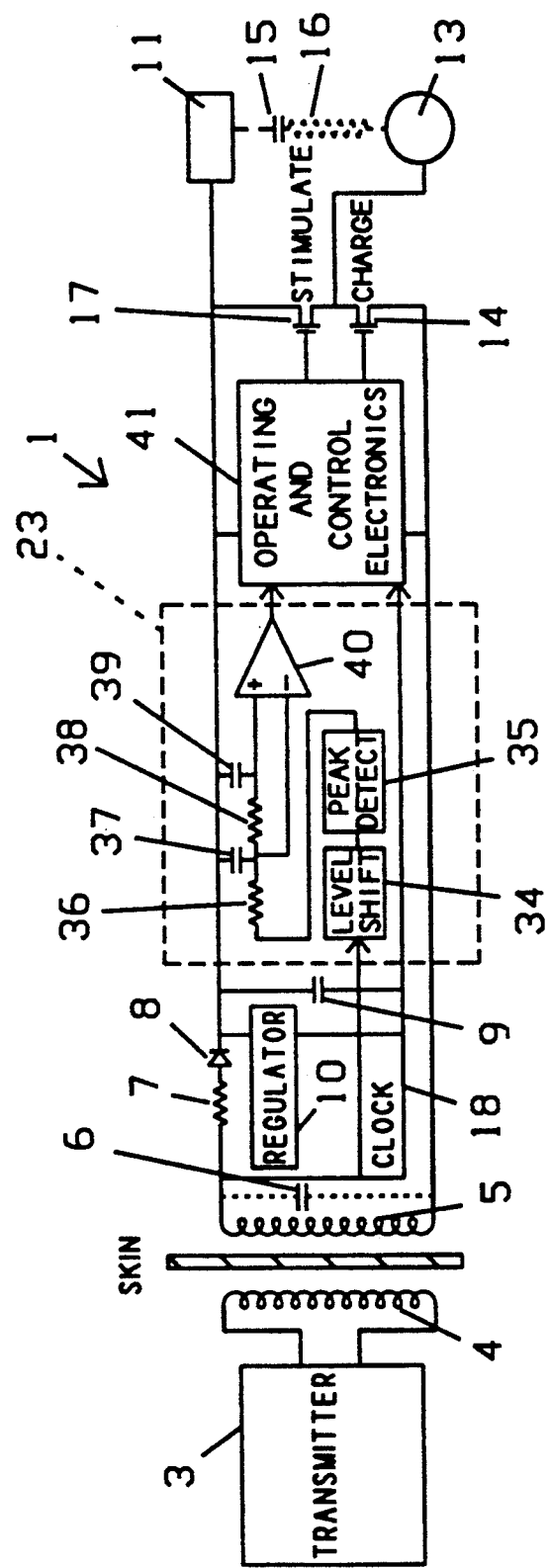
FIG. 5 is a schematic of an implantable stimulator having operating and control electronics, which, in turn, is under the control of a transmitter.

FIG. 5 illustrates an implantable stimulator 1 having operating and control electronics, which, in turn, is under the control of transmitter 3. Demodulator 33 is comprised of level shift 34, which is connected to receive the energy received by the receiving coil 11 and drops the peaks to a detection range so the peak detector 35 can detect the peaks. From that detected signal, a short term detected signal is obtained by resistor 36 and capacitor 37 and a long term average detected signal is obtained by resistor 38 and capacitor 39 (which have a longer time constant than the first resistor and capacitor). The short term detected signal and the long term average detected signal are fed into comparator 40 which provides the detected data to be Processed by the operating and control electronics 41. Similarly to logic 12 in FIG. 1, operating and control electronics 41 in FIG. 2 controls the charge and discharge (stimulation) of the electrodes 11 and 13. Synchronization of the operating and control electronics with other devices, and within the device itself, is obtained by a clock signal on line 18, derived from the alternating field received by coil 5.

Figure 6:
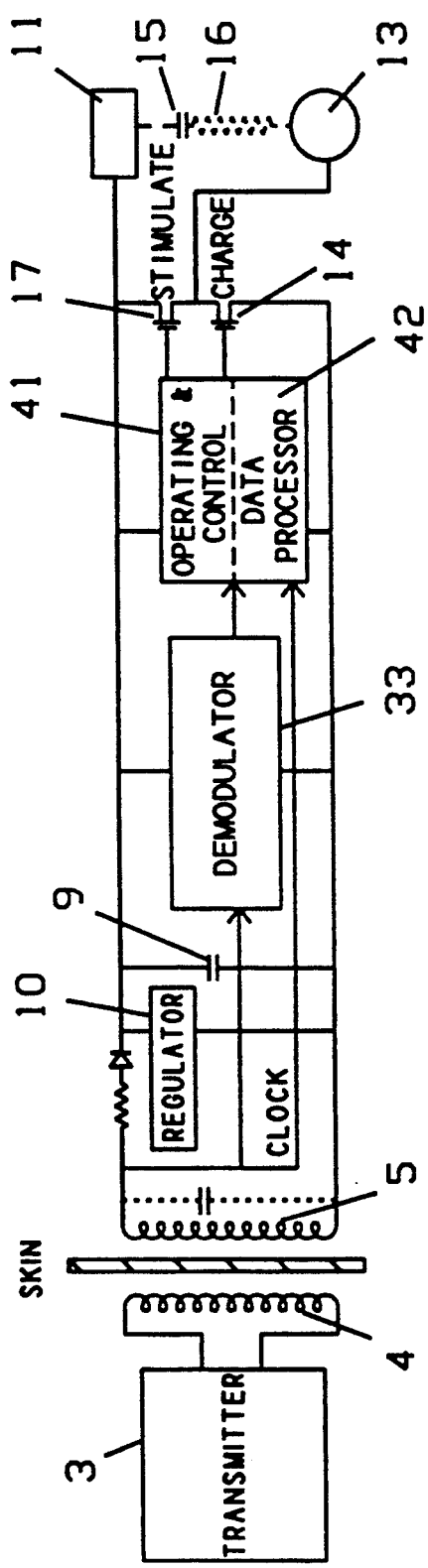
FIG. 6 is a schematic of an implantable stimulator having operating and control electronics comprising a data processor.

FIG. 6 is a schematic of an implantable stimulator 1 having operating and control electronics 41 comprising a data processor 42. Demodulator 33 as well as operating and control electronics 41, including data processor 42 obtain their electrical operating voltage from energy stored on capacitor 15.

Electrolytic electrode 11 and counterelectrode 13 provide sufficient storage capability for electrical energy to power the stimulation control electronics 41, including the data processor 42, if there be one. The current flow at which electrolytic electrode 11 stores electrical energy, for example, might be 10 to 100 microamperes. The output current flow provided by electrolytic electrode 11 might be, for example, 2 to 30 ma. Thus, the output rate of current flow provided by electrolytic electrode 11, to energize the internal electrical circuitry, may well be on the order of several hundred times the rate of current flow received by the implanted device.

The alternating magnetic field transmitted to coil 5 may be modulated or encoded, as is commonly known within the art, with instructions to the stimulator as to pulse duration, time of stimulation, amplitude, and pulse shape. The data processor 42 would determine such instructions and pass the information along to the remaining operating and control electronics portion. Operating and control electronics 41 controls the restoration of the charge on capacitor 15 by means of transistor switch 14. Operating and control electronics 41 controls the discharge of the charge on capacitor 15 by means of transistor switch 17. In all likelihood, when transistor switch 17 is closed, (to discharge, or partially discharge capacitor 15), transistor switch 14 would be open to isolate electrode 14 from the voltage supply line.

It may be appreciated that methods other than induction or other electromagnetic transmission of energy may be used to charge the electrolytic capacitor of the invention. The electrolytic capacitor may be charged by a direct wire connection which runs transcutaneously to an external power source or, on the other hand, by a direct wire connection which extends within the body to a power source which is also implanted. It is intended to include such all such additional means of providing electrical energy which may be stored by the electrolytic capacitor. The invention relates to the electrolytic storage of such energy, not in the sources of electrical energy, which may vary widely.

Although specific embodiments and certain structural and electrical arrangements have been illustrated and described herein, it will be clear to those skilled in the art that various other modifications and embodiments may be made incorporating the spirit and scope of the underlying inventive concepts and that the same are not limited to the particular forms herein shown and described except insofar as determined by the scope of the appended claims.

I claim:

1. In an implantable device, means for receiving electromagnetic energy and to convert such electromagnetic energy to electrical energy, internal electrical circuitry, capacitor means connected to receive and store at least a portion of said electrical energy and connected to provide at least a portion of said stored energy to said internal electrical circuitry, and wherein said capacitor means comprises an electrolytic, capacitive electrode adapted for disposal at least partially in body fluids.

2. The device as recited in claim 1 in which said device comprises stimulating means and in which said capacitor means comprising said electrolytic electrode provides the electrical energy for the stimulation.

3. The device as recited in claim 1 in which said capacitor means comprises sufficient capacitance to store sufficient electrical energy and is connected to provide electrical current to said internal electrical circuitry at rates substantially in excess of the rate at which electrical current is received by said implantable device.

4. The implantable device recited in claim 1 in which said internal electrical circuitry comprises one or more of operating electronics and control electronics for said implantable device and said capacitor means provides electrical energy for the operation of at least a portion of said internal electrical circuitry.

5. The implantable device recited in claim 1 in which said internal electrical circuitry comprises data processing means and said capacitor means provides electrical energy for the operation of at least a portion of said data processing means.

6. The implantable device recited in claim 1, in which said electrode is of a porous material comprised of an electrically-conductive material.

7. The implantable device recited in claim 6, wherein said electrode is anodized, porous tantalum.

8. The implantable device recited in claim 1, wherein said electrode has a high surface-to-volume ratio.

9. The implantable device recited in claim 1, wherein said capacitor means comprises a second electrode adapted for disposal at least partially in body fluids, and wherein is included circuit means connecting said second electrode as a counterelectrode to said electrolytic, capacitive electrode.

10. The implantable device recited in claim 9, wherein said second electrode is comprised of activated iridium.

11. The implantable device recited in claim 10, wherein said electrolytic electrode is anodized, porous tantalum.

12. In an implantable device, means for receiving electrical energy, internal electrical circuitry, capacitor means connected to receive and store at least a portion of said energy as an energy source for at least a portion of said internal electrical circuitry of said device, and wherein said capacitor means comprises an electrolytic, capacitive electrode connected to provide at least a portion of said electrical energy to said internal electrical circuitry and adapted to be disposed at least partially in body fluids.

13. The device recited in claim 12, wherein said capacitor means further comprises a counterelectrode adapted to be disposed at least partially in body fluids.

14. The device recited in claim 12, wherein said internal electrical circuitry comprises one or more of operating electronics, data processing electronics, and control electronics.

15. The device recited in claim 12, wherein said electrode is comprised of a porous metal.

16. The device recited in claim 13, wherein one of said electrodes is comprised of anodized, porous metal and the other is comprised of activated iridium.

17. The device recited in claim 12, wherein said electrode is comprised of activated iridium.

18. The device recited in claim 12, wherein said capacitor means is connected to provide electrical energy at rates in excess of that at which it receives and stores said electrical energy.

19. In an implantable device, internal electrical circuitry, means for receiving electrical energy, capacitor means connected to receive electrical energy from said means for receiving electrical energy and connected to store at least a portion of said electrical energy, and wherein said capacitor means is connected to provide energy for at least a portion of said internal electrical circuitry of said device, and wherein said capacitor means comprises at least one electrolytic, capacitive electrode and a counterelectrode, each adapted to be disposed at least partially in body fluids, and wherein said electrodes are connected and adapted to provide stimulating pulses to the body.

20. The implantable device recited in claim 19 in which said device is of a size implantable through a hypodermic needle.

21. The implantable device recited in claim 19 in which in included means for charging said capacitor means to a voltage substantially beyond the voltage required for said stimulating pulses.

22. The implantable device recited in claim 19 is which said capacitor means is connected to provide energy to said internal electrical circuitry at rates substantially in excess of the rate at which it receives and stores such energy from said means for receiving electrical energy.

23. In an implantable device, means for receiving electromagnetic energy and to provide therefrom electrical energy, capacitor means connected to receive and store at least a portion of said electrical energy, said capacitor means connected to provide electrical energy for said implantable device, and wherein said capacitor means comprises an electrolytic, capacitive electrode adapted to be at least partially disposed in body fluids.

24. The implantable device recited in claim 23 in which is included means for charging said capacitor means with a substantially larger amount of electrical energy than is required for said stimulation pulses.

25. The implantable device recited in claim 24 in which said device is of a size implantable through a hypodermic needle.

26. The implantable device recited in claim 23 in which said device comprises electrical stimulation means for providing electrical stimulation and said capacitor means is connected to provide the energy for said electrical stimulation.

27. The implantable device recited in claim 26 in which said capacitor means further comprises a counterelectrode and said counterelectrode is adapted to be at least partially disposed in body fluids and thereby provide a resistive path through said body fluids between said counterelectrode and said electrolytic, capacitive electrode, said counterelectrode connected to be oppositely charged from said electrolytic, capacitive electrode and wherein is included means for charging said capacitor means to a voltage sufficient to drive a stimulating current pulse through said resistive path.

28. The implantable device recited in claim 26 in which is included means for charging said capacitor means to a voltage substantially beyond the voltage required for said stimulation.

29. The device recited in claim 23 wherein said device comprises electrical stimulation means and said capacitor means is connected to provide energy to said electrical stimulation means and wherein said electrolytic, capacitive electrode is connected to be a stimulating electrode of said electrical stimulation means.

30. The device recited in claim 23 in which is included counterelectrode means adapted to be at least partially disposed in body fluids, said counterelectrode being connected to be charged oppositely from said electrolytic, capacitive electrode and means for connecting said electrodes to provide an electrical path for causing stimulating pulses in said body fluids between said electrodes.

31. The device recited in claim 30 in which said counterelectrode is a non-polarizing metal.

32. The device recited in claim 31 in which said non-polarizing metal is iridium.

33. The device recited in claim 30 in which said electrolytic electrode is anodally operated and said counterelectrode is cathodally operated and wherein said counterelectrode, when said electrodes are charged, is at approximately $-0.4$ volts vs. standard calomel electrode and the remainder of the potential between said electrodes appears as the potential of the electrolytic electrode.

34. The device recited in claim 30 in which said electrolytic electrode is anodized, porous tantalum and said counterelectrode is activated iridium.

35. The device recited in claim 30 wherein is included an electrical circuit between said two electrodes for at least partially discharging said electrodes and wherein is included means for controlling the flow of current in said electrical circuit between said two electrodes.

36. In an implantable device, internal electrical circuitry, said device further comprising capacitor means for storing electrical energy, said capacitor means comprising an electrolytic, capacitive electrode, said electrode adapted to be disposed at least partially in body fluids and wherein said capacitor means is connected to provide at least a portion of the electrical energy utilized by said implantable device.

37. The method of storing electrical energy in an implanted device for providing at least a portion of the electrical energy for said device, comprising providing an electrolytic, capacitive electrode disposed at least partially in body fluids and storing said electrical energy by charging said electrolytic, capacitive electrode, and discharging said electrolytic, capacitive electrode to provide said electrical energy.

38. The method of claim 37 including the step of utilizing said electrical energy provided in discharge of said electrolytic, capacitive electrode to provide electrical stimulation, and wherein is included the step of charging said electrolytic, capacitive electrode to a voltage substantially greater than the voltage required for said stimulation.

* * * * *